US011779944B2

(12) United States Patent
Gerde (10) Patent No.: US 11,779,944 B2
(45) Date of Patent: Oct. 10, 2023

(54) APPARATUS AND METHOD FOR GENERATING AN AEROSOL

(71) Applicant: INHALATION SCIENCES SWEDEN AB, Novum (SE)

(72) Inventor: Per Gerde, Trosa (SE)

(73) Assignee: INHALATION SCIENCES SWEDEN AB, Novum (SE)

( * ) Notice: Subject to any disclaimer, the term of this patent is extended or adjusted under 35 U.S.C. 154(b) by 154 days.

(21) Appl. No.: 17/097,052

(22) Filed: Nov. 13, 2020

(65) Prior Publication Data

US 2021/0060591 A1 Mar. 4, 2021

Related U.S. Application Data

(62) Division of application No. 14/906,701, filed as application No. PCT/SE2014/050895 on Jul. 16, 2014, now Pat. No. 10,850,289.

(30) Foreign Application Priority Data

Jul. 22, 2013 (SE) .................................. 1350907-0

(51) Int. Cl.
*B05B 7/14* (2006.01)
*A61M 15/00* (2006.01)
(Continued)

(52) U.S. Cl.
CPC .......... *B05B 7/1486* (2013.01); *A61K 9/0073* (2013.01); *A61M 15/009* (2013.01);
(Continued)

(58) Field of Classification Search
CPC ..... B05B 7/1486; B05B 1/262; A61K 9/0073; A61M 15/009; A61M 15/00; A61M 2202/064
See application file for complete search history.

(56) References Cited

U.S. PATENT DOCUMENTS 3,653,380 A   4/1972   Hansen
4,069,819 A   1/1978   Valentini et al.
(Continued)

FOREIGN PATENT DOCUMENTS

EP   0477222 A1   2/2007
EP   1028815 B1   3/2012
(Continued)

OTHER PUBLICATIONS

Search Report dated Feb. 20, 2017 from corresponding European Application No. 14829942.3.

*Primary Examiner* — Qingzhang Zhou
(74) *Attorney, Agent, or Firm* — Porter Wright Morris & Arthur LLP (57) ABSTRACT

The present invention is directed to improvements related to the generation of aerosols and outlines an apparatus and methods which supports deagglomeration and counteracts reagglomeration of aerosol particles. The apparatus is provided with an arrangement of inlet conduits for pressurized gas that promote transportation with a rotational flow towards an exit conduit. In order to further support production of high quality aerosols, the apparatus can be provided with an impactor aligned with the exit conduit with at least one impacting surface that minimizes formation of impact residues.

16 Claims, 4 Drawing Sheets

(51) Int. Cl.
   *A61K 9/00* (2006.01)
   *B05B 1/26* (2006.01)
(52) U.S. Cl.
   CPC ............. *B05B 1/262* (2013.01); *A61M 15/00* (2013.01); *A61M 2202/064* (2013.01)

(56) References Cited

U.S. PATENT DOCUMENTS

| | | | |
|---|---|---|---|
| 4,446,862 A | 5/1984 | Baum et al. | |
| 5,458,135 A | 10/1995 | Patton et al. | |
| 5,458,136 A * | 10/1995 | Jaser | A61M 15/00 |
| | | | 128/200.14 |
| 5,785,049 A | 7/1998 | Smith et al. | |
| 5,997,848 A * | 12/1999 | Patton | A61P 3/08 |
| | | | 514/6.9 |
| 6,347,629 B1 | 2/2002 | Braithwaite | |
| 6,415,790 B1 | 7/2002 | Leedom et al. | |
| 2005/0279349 A1 | 12/2005 | Patton et al. | |
| 2007/0051835 A1 | 3/2007 | Yasui et al. | |
| 2008/0115785 A1 | 5/2008 | Eason et al. | |
| 2009/0001198 A1 | 1/2009 | Norimatsu | |
| 2009/0191349 A1 | 7/2009 | Norimatsu | |
| 2009/0260623 A1 * | 10/2009 | Dunkley | A61M 15/0028 |
| | | | 128/200.23 |
| 2010/0327075 A1 | 12/2010 | Biddle | |
| 2011/0094507 A1 | 4/2011 | Wachtel et al. | |
| 2011/0100560 A1 | 5/2011 | Gerde | |
| 2013/0000640 A1 | 1/2013 | Maynard et al. | |
| 2013/0047985 A1 | 2/2013 | Harris et al. | |
| 2014/0053831 A1 * | 2/2014 | Leamon | A61M 11/042 |
| | | | 128/200.14 |

FOREIGN PATENT DOCUMENTS

| | | |
|---|---|---|
| JP | 61-249532 A | 11/1986 |
| WO | 90/15635 A1 | 12/1990 |
| WO | 99/25484 A1 | 5/1999 |
| WO | 02/056948 A1 | 7/2002 |
| WO | 03/024610 A1 | 3/2003 |
| WO | 2008/017575 A1 | 2/2008 |
| WO | 2013/036881 A2 | 3/2013 |
| WO | 2013/090841 A2 | 6/2013 |

* cited by examiner

APPARATUS AND METHOD FOR GENERATING AN AEROSOL

FIELD OF THE INVENTION

The present invention is directed to improvements related to the generation of aerosols and outlines devices and methods which support deagglomeration and counteract reagglomeration of aerosol particles.

BACKGROUND OF THE INVENTION

European patent specification EP 1 028 815 describes an apparatus that effectively generates batches of high quality aerosols from dry powder. Such aerosols can be received in a vertically connected holding chamber and transported to a target, as exemplified in WO 2009/002267.

The apparatus of EP 1 028 815 operates by using the energy in a compressed gas to break up the powder in a powder chamber where the powder is instantaneously pressurized and suspended, whereupon a turbulent non-rotating flow transports the powder for ejection through a narrow exit conduit leading to the holding chamber. The rapid expansion from the narrow exit conduit accomplishes deagglomeration and generation of a micrometer size aerosol with a controlled, narrow size distribution. Even if this technology gives excellent results for a broad range of powder qualities, there are certain powder materials which are exceedingly cohesive due to mechanisms like van der Waal forces, electrostatic interaction and capillary condensation of humidity in hygroscopic material. Apart from impaired control of the aerosol particle size distribution this may lead to immediate problems in the process from clogging and material losses. The present invention aims at improving the discussed technology of aerosolization by boosting the de-agglomeration of aerosolized powders.

US 2009/0191349 discloses an aerosol generator wherein the powder accommodated in a generator vessel with a number of differently directed jetting ports that stationary de-aggregates and fluidizes the powder. In order to generate a transported aerosol, a supply gas introduced from below a porous pate to transport an aerosol with classified particles to an outlet. US 2009/0260623 discloses a hand held aerosol generator with a rotating powder capsule and a number of angled air inlet ports for aerosol generation by the user. U.S. Pat. No. 6,415,790 discloses another hand held aerosol generator wherein powder released from specifically designed blisters are transported to the inhaling user by turbulence from air inlet channels. None of these documents provide any particular means for counteracting particles of the generated aerosol to agglomerate. WO 02/056948 discloses and inhaler with an aerosol generator and an impact member with flat round surface surrounded by a conical surface facing the aerosol stream. Even if the impact member promotes deagglomeration, its position and construction may risk accumulation of adhesive powder particles in the region of the flat apex of the impactor member.

It is evident that there is a need for an aerosol generator that is adapted also for powders with adhesive particles with high tendency to agglomerate that is capable of effectively transporting the aerosol while promoting deagglomeration in order to provide aerosols with improved better controlled particle size and thereby obtain improved dose accuracy for inhalable aerosolized products.

DESCRIPTION OF THE INVENTION

In general terms, the present invention is directed to an apparatus and a method of generating aerosol doses from a dry powder source with a highly pressurized gas and thereby provide means that improve aerosol quality and the load capacity also from powders with a strong cohesiveness and a great ability to withstand deagglomeration.

The present invention is directed to an aerosol generating apparatus comprising an at least partially spherical powder chamber for loading and mixing powder with pressurized gas, having one or several compartments, at least two pressure conduits operably connected to a pressure chamber for introducing pressurized gas to the powder chamber by at least two inlet orifices and an ejection conduit opening at an exit orifice to ambient pressure. The apparatus is further characterized in that it has a main axis of rotational symmetry, in that the at least two inlet conduits have each a symmetry axis extending into projection lines and are arranged to admit inlet flows in opposite directions, in that the inlet conduit projection lines are equidistant to a plane which contains the apparatus main axis of symmetry termed the inlet conduit parallel plane, and in that the inlet conduit projection lines form acute angles with the apparatus main axis of rotational symmetry. In one aspect the acute angles are in the approximate range of 35 to 70 degrees and the acute angles can have the same or different values. In accordance with the invention, the at least two inlet orifices are admitted to introduce pressurized gas "off-set" to the apparatus main axis of symmetry, in opposite directions, so a powerful rotating flow towards the exit conduit will become established. The apparatus is further characterized in that the at least two inlet conduits have inlet orifices located the at least partially spherical part of the powder chamber. In the context of the present invention the term "at least partially" spherical has the meaning of a full sphere or any fraction of a sphere, such as a hemisphere, In one aspect, the powder chamber comprises an essentially spherical compartment comprising at least two inlet orifices for pressurized gas.

In accordance with one aspect the invention, the apparatus can be loaded batch-wise with aerosolizable powder. According to another aspect, the apparatus can be provided with arrangements that admit a plurality of discreet powder compositions to be aerosolized, simultaneously and/or sequentially. As an example the powder compositions can arranged in displaceable blisters packages and similar multi-compartment containers.

In one aspect the powder chamber comprises an essentially hemispherical compartment comprising at least two inlet orifices for pressurized gas.

In one aspect, the powder chamber comprises a substantially cylindrical compartment, a substantially ellipsoid compartment and the ellipsoid compartment comprises the ejecting conduit. By way of an advantageous example, the apparatus can comprise a hemispherical part arranged with the at least two inlet conduits, a cylindrical midsection and an ellipsoidal upper section with the exit conduit.

In one aspect of the invention, the apparatus has a minimum distance between the inlet conduit projection lines and the inlet conduit parallel plane that is from about 0.01 to about 1 mm.

In one aspect, the apparatus is provided with an ejecting conduit having an abrupt inlet. The ejecting conduit can have a substantially uniform cross-section, essentially shaped as a cylinder. The definition of an abrupt inlet is further outlined in European patent specification 1028815.

In one aspect, the apparatus is provided with at least two inlet conduits which are essentially cylindrical and the inlet orifice is configured as an ellipsoid.

The apparatus according to the different aspects of the invention can further at least one additional inlet conduit with a projection line that intersects the inlet conduit parallel plane.

In one further aspect, the invention relates to an aerosol generating apparatus comprising a powder chamber for loading and mixing powder with pressurized gas, at least two pressure conduits operably connected to a pressure chamber for introducing pressurized gas to the powder chamber by at least two inlet orifices and an ejection conduit opening at an exit orifice to ambient pressure. The ejection conduit preferably has an abrupt inlet as defined in European patent specification 1028815 and at least two inlet conduits may be arranged with the previously defined off-set arrangement and other described definitions. According to this aspect, the apparatus comprises an impactor adapted to meet the powder discharged from the exit orifice, by being aligned with the ejection conduit in an impactor housing. Further according to this aspect, the impactor comprises an impactor body having an impacting surface and between the impactor body and an impactor housing, an impactor channel or slit is provided with a substantially ring-shaped shaped cross-section. Still further according to this aspect, the impactor body comprises a conical part wherein said conical part provides a primary impacting surface and a substantially cylindrical part. The impactor body is accommodated in an impactor housing and arranged so that the annular axially extended channel or slit is provided between the impactor body and the impactor housing. The entrance region of the annular axially extended slit comprises a secondary impaction surface. The secondary impact surface is provided at the cylindrical inner surface of the cylindrical part of the impactor housing. The housing is dimensioned and arranged to receive the aerosol delivered from ejection orifice in a manner that counteracts pile-up of material and secures exposure to the impacting surface. The annular slit is thus arranged to comprise both a secondary impacting surface and to retard the aerosol flow in order to contribute to an additional break-up of agglomerates.

In one aspect, the conical part of the impactor body is a recessed cone comprising a surface with a tangent having an angle with the main axis of symmetry that increases with the cone radius, admitting essentially the same acute impact angle for each powder agglomerate meeting the impacting surface. The so curved impactor surface provides for avoiding impact angles close to perpendicularly in order to avoid impact residues of material to form and accumulate and thereby potentially decrease deagglomeration capacity of the apparatus. By means of the curved impactor surface and the narrow annular slit deagglomeration is performed in two stages and at different sites of the impactor which contribute to significant improvements in counteracting reagglomeration and provide for a controlled aerosol particle size also for particles with adhesive characteristics. For this reason, it is advantageous that the slit is designed with suitable width considering both desirable aerosol exit velocity and complementary impacting effect when counteracting deagglomeration. In one aspect the slit has width of 0.2 mm or less such 0.2 mm, 0.1 mm, 0.15 mm, or 0.005 mm.

In another aspect, the invention relates to a method of generating an aerosol. The method comprises the steps of loading a powder chamber with an aerosolizable powder; releasing a pressurized gas and introducing it into an at least partially spherical part of the powder chamber by at least two pressure conduits with inlet orifices and providing a suspension of mixed gas and powder; establishing a rotating flow of the suspension in at least one compartment of said powder chamber; admitting the flow of the suspension to establish along the powder chamber inner walls to an ejection conduit of the powder chamber;

admitting the suspension to form an aerosol in an ejection nozzle and subjecting it to at least one impacting surface and transporting it to through a substantially ring-shaped impactor channel; and providing and optionally collecting the so formed aerosol.

In one aspect of the method the pressurized gas has a pressure of at least 50 bar, for example about 100 bar. The pressurized gas will then be able to become introduced at a sonic velocity and by arranging at least two inlet conduits according to what has been defined above, a powerful rotating flow of suspension powder in gas can be established. In one aspect, the rotating flow is established in at least a substantially hemispherical compartment of the powder chamber.

In one aspect of the method, the aerosol particles meet a primary impactor surface at essentially the same impact angle in order to minimize the risk of obtaining impact residues on the surface.

In one aspect of the method, subsequent to the first impacting surface, the stream of aerosol particles meet a secondary impacting surface at an essentially non-perpendicular angle. In this aspect the primary and secondary surfaces are defined according to the previous parts of the specification.

The invention according to the described aspects has by providing a feed of the loaded powder with a rotating flow towards the exit conduit, two major advantages: I) The more gradual feed of material induced by the rotation substantially decrease the risk of clogging the exit conduit at the narrowest part. II) The more gradual feed of material toward an impactor surface in the exit conduit decreases, the risk of agglomerates impacting on each other rather than on the hard impactor surface. This increases the load capacity of the aerosol generator at a maintained aerosolizing ability.

DETAILED DESCRIPTION OF THE INVENTION

Before the invention is disclosed and described in detail, it is to be understood that this invention is not limited to particular compounds, configurations, method steps, substrates, and materials disclosed herein as such compounds, configurations, method steps, substrates, and materials may vary somewhat.

It is also to be understood that the terminology employed herein is used for the purpose of describing particular embodiments only and is not intended to be limiting since the scope of the present invention is limited only by the appended claims and equivalents thereof.

If nothing else is defined, any terms and scientific terminology used herein are intended to have the meanings commonly understood by those skilled in the art to which this invention pertains.

It must be noted that, as used in this specification and the appended claims, the singular forms "a", "an" and "the" include plural referents unless the context clearly dictates otherwise.

The term "about" as used in connection with a numerical value throughout the description and the claims denotes an interval of accuracy, familiar and acceptable to a person skilled in the art. Said interval is ±10%.

Other features and uses of the invention and their associated advantages will be evident to a person skilled in the art upon reading the description and the examples.

It is to be understood that this invention is not limited to the particular embodiments shown here. The following examples are provided for illustrative purposes and are not intended to limit the scope of the invention since the scope of the present invention is limited only by the appended claims and equivalents thereof.

The following definitions include terms used in the detailed description of the invention, but are also valid for the same terms in any earlier general description of the invention and the appended claims. Certain terms are also defined in the general, earlier contexts of the description.

A powder chamber is the chamber set to accommodate the powder to be aerosolized. The powder camber be essentially spherical or have other symmetrical shapes.

An inlet conduit is a conduit for transporting pressurized gas to the powder chamber and may include one or more releasable valves to be released when charging the apparatus. The inlet conduit or conduits terminate with an inlet orifice to the powder chamber.

An ejection conduit is an exit conduit of the powder chamber for discharging the mixture of powder and pressurized air from the powder chamber. The ejection conduit terminates with an ejection orifice to ambient air.

The main axis of rotational symmetry of the apparatus is the axis of symmetry the apparatus through the exit nozzle of the apparatus. An infinite number of symmetry planes can be defined to be aligned with and containing the rotational axis of symmetry and intersecting each other at arbitrary angles.

An inlet conduit projection line coincides with the axial symmetry line of the essentially cylindrical inlet conduit extends from inlet orifice into the powder chamber. Inlet conduit projection lines of the at least two inlet orifices are equidistant to a plane which contains the main axis of rotational symmetry of the apparatus termed inlet conduit parallel plane.

Off-set distance is the distance between the inlet conduit projection lines and the inlet conduit parallel plane. The off-set distance is >0. The projection lines of at least two inlet orifices for pressurized gas are off-set from the main axis of rotational symmetry. Accordingly, the projection lines of further, additional inlet orifices may lie within one single plane of symmetry and intersect the projection line through the exit orifice.

An acute angle is an angle less than about 70 degrees, preferable less than 60 degrees. An acute angle is formed between the inlet conduit projection lines and the main axis of rotational symmetry of the apparatus.

An impact angle is the angle between the path of aerosol particle or an agglomerate of aerosol particle travelling from the ejection orifice and onto the impactor surface.

Figure 1:
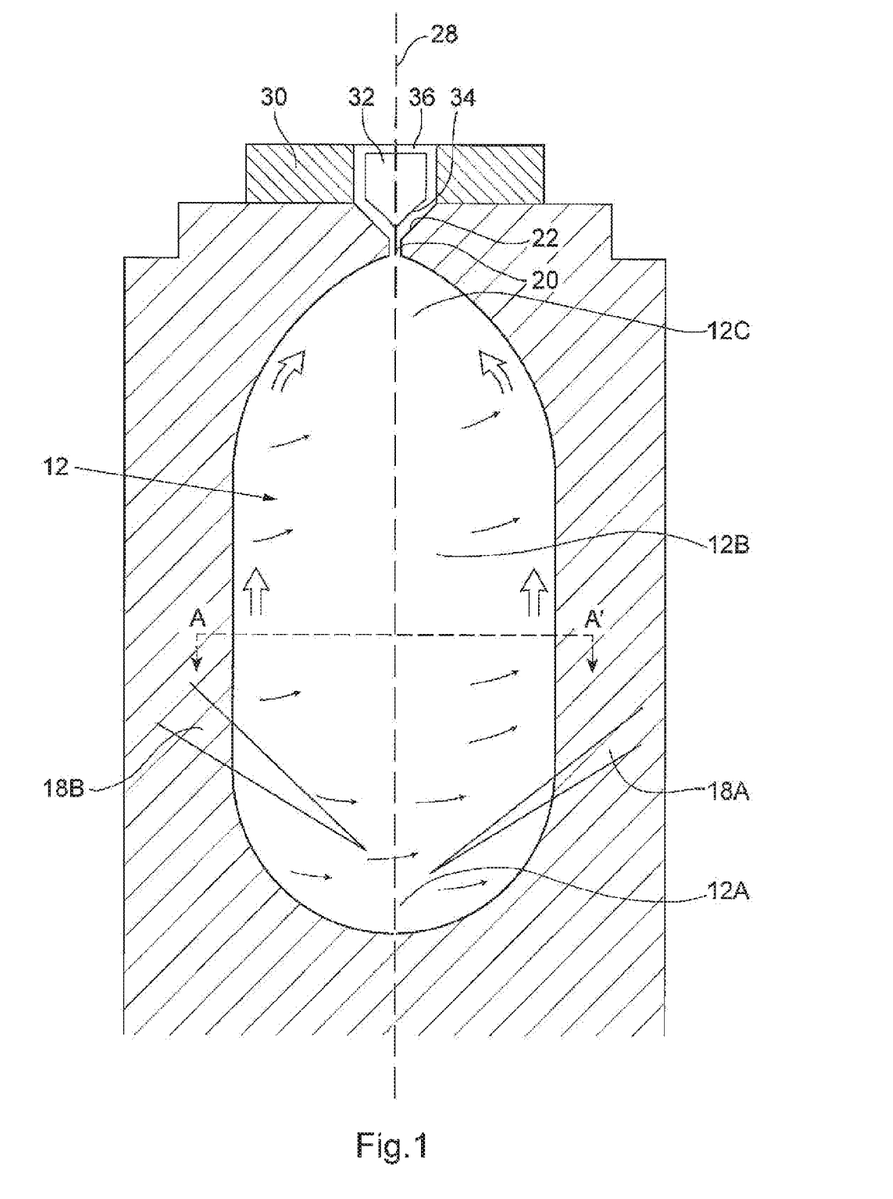
FIG. 1 shows an aerosol generator according to the invention through a section representing a plane of symmetry with the inlet orifices for pressurized gas schematically shown.

FIG. 1 shows the apparatus 10 in a section according to a symmetry plane with a main axis of rotational symmetry 28. The powder chamber 12 has a hemispherical part 12B, a cylindrical part 12B and an ellipsoidal part 12C. The apparatus can be accommodated in housing or a similar arrangement. In FIG. 1 the two inlet conduits 18A and 18B and their orifices are only schematically shown and it is referred to FIG. 2 that is a view from above from section A-A' in FIG. 1 for their arrangements. FIG. 1 further schematically shows the ejection conduit 20 with its ejection orifice and the impactor arrangement 30. The impactor arrangement 30 comprises an impactor body 32, a ring shaped impactor channel 36 providing an annular slit surrounding the impactor body 32. The impactor body 32 is provided with a cylindrical part and a conical part that will be described in more detail in the context of FIG. 4. FIG. 1 further illustrates the rotating flow established by the pressurized gas from the inlet conduits and how a flow is established forwards along the powder chamber inner walls towards the ejection conduit.

Figure 2:
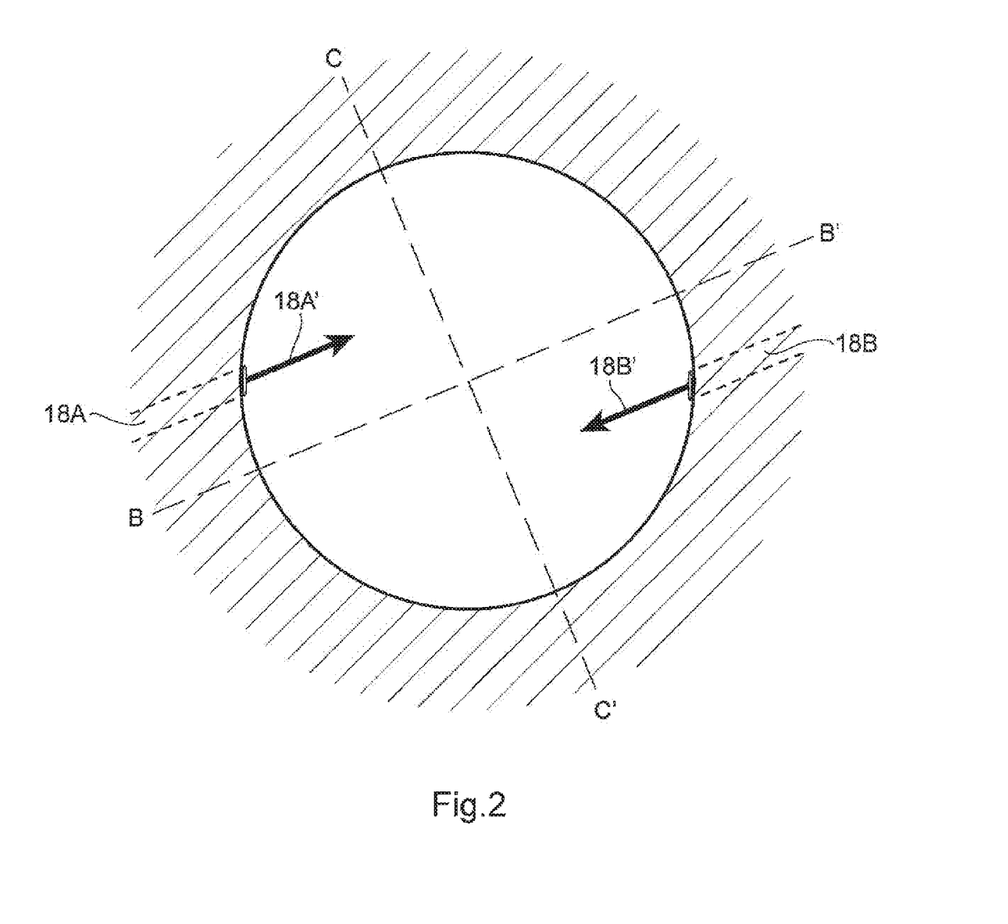
FIG. 2 shows the aerosol generator with the inlet orifices as viewed through plane A-A' in FIG. 1. Also indicated are the inlet conduit parallel plane B-B' and its normal plane C-C'.

The view from above along section A-A' in FIG. 1 is shown in FIG. 2 and demonstrates two oppositely arranged inlet conduits with inlet orifices to the powder chamber. FIG. 2 further shows inlet conduit projection lines 18A' and 18B', respectively which have the same distance to the inlet conduit parallel plane B-B'. This distance is between 0.01 to 1 mm. The inlet conduit parallel plane B-B' has a normal plane C-C' termed inlet conduit normal plane. The inlet conduits are cylindrically arranged and the inlet orifices are ellipsoidal with a largest dimension of in the range of about 0.5 to 1 mm. The exit orifice has a diameter in the range about 0.2 to 1 mm, in a powder chamber volume of about 1 ml. FIG. 2 also demonstrates the opposite direction of the inlet flows of pressurized gas.

Figure 3:
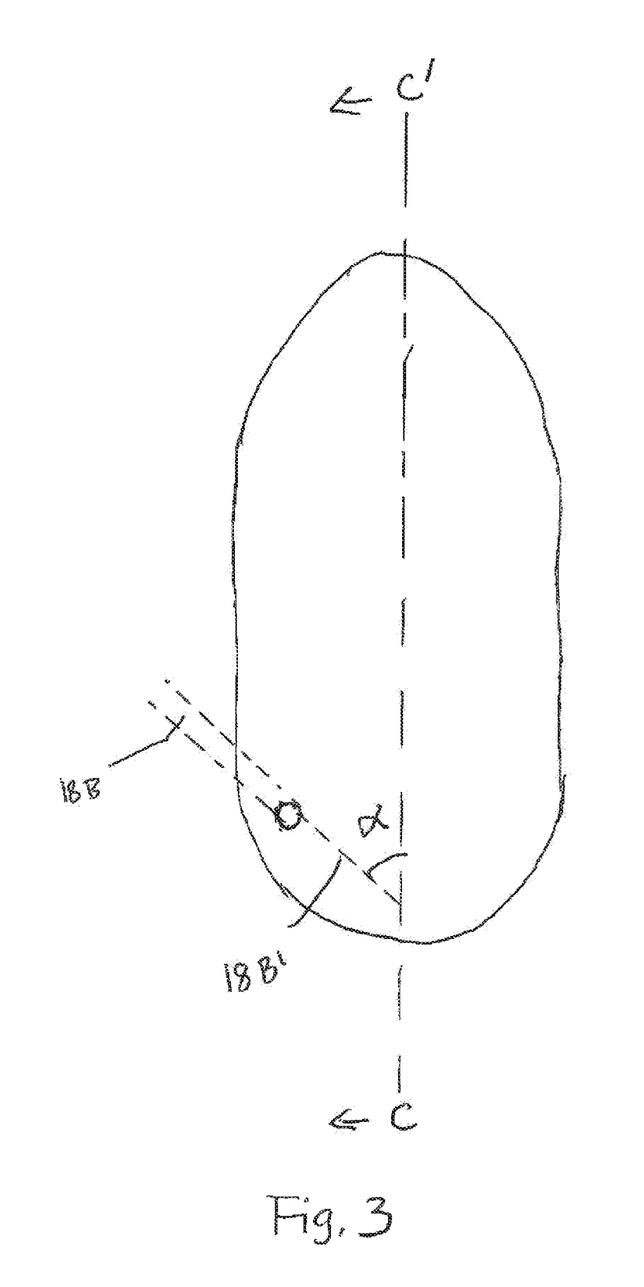
FIG. 3 shows a section of the apparatus, wherein the inlet conduit parallel plane B-B' is the plane of the paper demonstrating how a schematically shown inlet conduit projection line (shown in FIG. 2) has an angle α to the normal plane C-C'.

FIG. 3 further illustrates the angular arrangement of the inlet conduits, In FIG. 3 one inlet conduit projection line from inlet conduit 18B is depicted to form the acute angle α with the inlet conduit normal plane (C-C' in FIG. 2) that has a value in the range of 35-65 degrees. The other inlet orifice can be depicted in the same manner with an acute angle β. These angles can have the same or different acute values.

Figure 4:
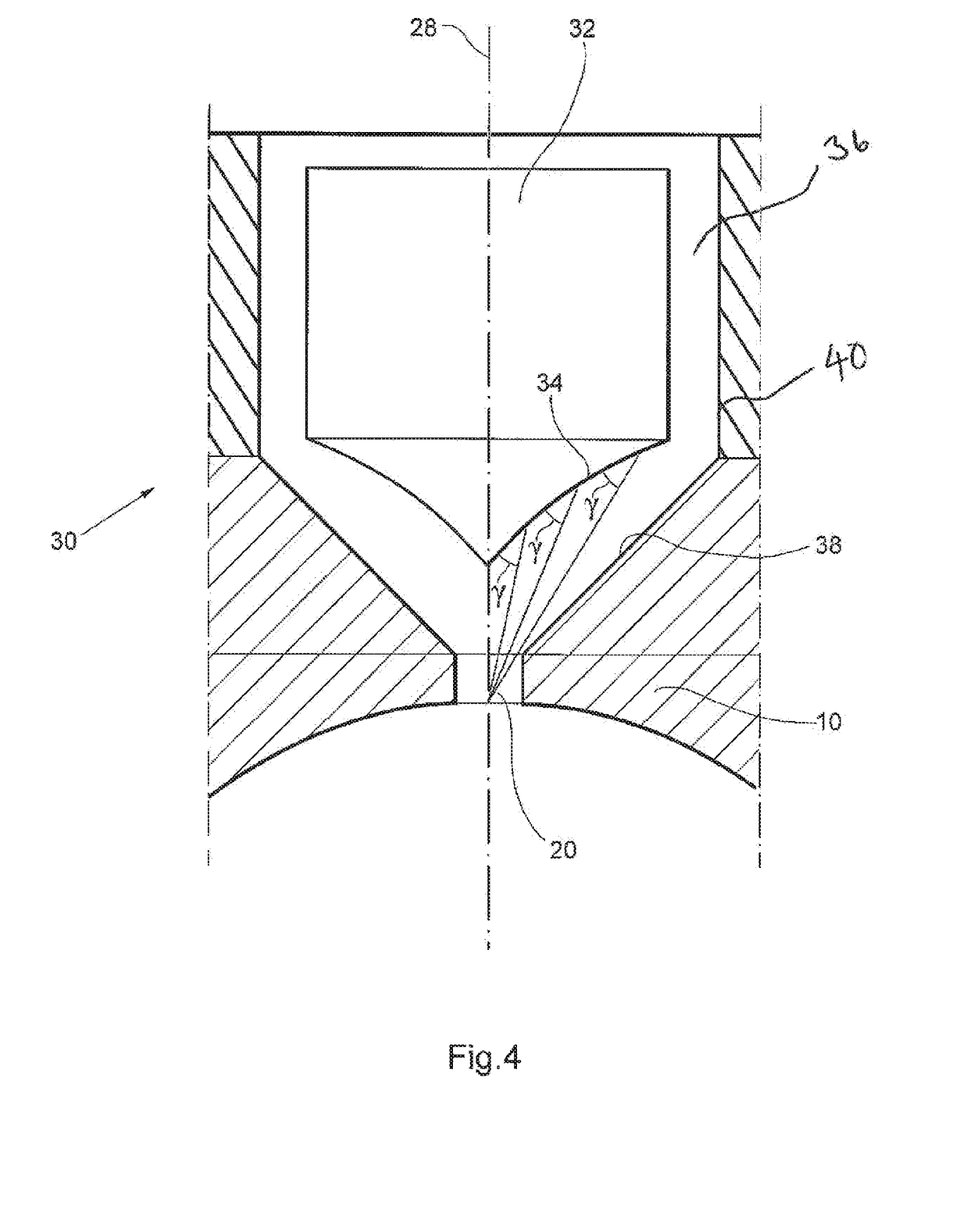
FIG. 4 shows the impactor and is housing in an enlargement of the arrangement of FIG. 1.

FIG. 4 is a detailed view of the impactor 30 in FIG. 1, showing the impactor accommodated in the impactor housing. The annular slit 36 surrounding the impactor body 32 has width of about of about 0.1 to 0.2 mm and the cylindrical part of the impactor body has diameter of 3-4 mm. The annular slit length is 2-3 mm. FIG. 4 further demonstrates the recessed cone of the impactor body with its curved primary impacting surface 34. It is schematically shown how agglomerates travel from the ejection conduit of the powder chamber and that the curvature of the impacting surface admits that a substantially constant acute impacting angle γ is maintained irrespectively of where the impacting surface is hit. It is also schematically shown how the tangent to the surface has an angle with the main axis of symmetry that increases with the cone radius of the recessed cone. The so arranged primary impacting surface 34 will counteract formation of impact residues which may form when agglomerates hit the primary impacting surface 34 perpendicularly or close thereto. The impactor housing 38 is dimensioned to counteract pile up of aerosolized material and is formed to admit the annular slit 36 to extend between the cylindrical part of the impactor body and to provide an inner surface of the cylindrical part of the impactor housing 38. A secondary impacting surface 40 is formed at the inner surface of the cylindrical part of the impactor housing in region of the entrance of the annular slit. In operation, powder (aerosol particles) will depart essentially tangentially from the primary impacting surface and hit the secondary impacting surface at an essentially non-perpendicular impacting angle. The aerosol flow rate will retard in the annular slit and the aerosol will be distributed form the impactor orifice as a well-defined aerosol plume. The described impactor with its complementary impacting surfaces provides a very efficient way of producing homogenous and well-defined aerosols arriving in a plume shape from the slit. It has been found that powders that have been regarded as difficult to handle by forming needle shaped crystals efficiently can be broken up by the apparatus according to the invention.

The invention claimed is:

1. An aerosol generating apparatus having a main axis of rotational symmetry and comprising:
    an at least partially spherical powder chamber for loading an aerosolizable a powder therein and mixing the aerosolizable powder with pressurized gas, the powder chamber having one or several compartments;
    at least two inlet conduits connected to a pressure chamber and being operable to introduce the pressurized gas to the powder chamber by at least two inlet orifices of said at least two inlet conduits, respectively, and create a powder suspension in the pressurized gas in the powder chamber; and
    an ejection conduit, the ejection conduit having an inlet from the powder chamber and opening at an exit orifice to an ambient pressure, the ejection conduit opening at the exit orifice being operable to form an aerosol when the powder suspension in the pressurized gas is released from the exit orifice, wherein
    (i) each of the at least two inlet conduits has a symmetry axis extending into a respective projection line and the at least two inlet conduits are arranged to admit pressurized gas inlet flows in opposite directions;
    (ii) the inlet conduit projection lines are equidistant to an inlet conduit parallel plane which contains the apparatus main axis of rotational symmetry;
    (iii) the inlet conduit projection lines form acute angles with the apparatus main axis of rotational symmetry; and
    (iv) the at least two inlet conduits have inlet orifices located in a spherical part of the at least partially spherical part of the powder chamber and operable to form a forward rotating flow of the powder suspension in the pressurized gas toward the ejection conduit inlet.

2. The apparatus according to claim 1, wherein the powder chamber comprises a substantially hemispherical compartment, comprising the at least two inlet orifices for pressurized gas.

3. The apparatus according to claim 1, wherein the powder chamber is spherical and wherein said inlet orifices are oppositely arranged in the powder chamber.

4. The apparatus according to claim 1, wherein the powder chamber further comprises a substantially cylindrical compartment and a substantially ellipsoid compartment.

5. The apparatus according to claim 4, wherein the substantially ellipsoid compartment comprises the ejection conduit.

6. The apparatus according to claim 1, wherein a distance between each of the conduit projection lines and the inlet conduit parallel plane is from about 0.01 to about 1 mm.

7. The apparatus according to claim 1, wherein the ejection conduit has a non-tapered abrupt inlet.

8. The apparatus according to claim 1, wherein the ejection conduit has a substantially uniform cross-section, substantially shaped as a cylinder.

9. The apparatus according to of claim 1, further comprising an impactor adapted to meet the aerosol powder discharged from the exit orifice.

10. The apparatus according to claim 9, wherein the impactor comprises an impactor body having an impacting surface and, between the impactor body and an impactor housing, an impactor channel is provided with a substantially ring-shaped shaped cross-section.

11. The apparatus according to claim 1, wherein the at least two inlet conduits are each substantially cylindrical, and the at least two inlet orifices are each an ellipsoid.

12. The apparatus according to claim 10, wherein the impactor body comprises a substantially cylindrical part and a conical part and wherein said conical part provides a primary impacting surface.

13. The apparatus according to claim 12, wherein the impactor further comprises a secondary impacting surface provided at a cylindrical inner surface of a cylindrical part of the impactor housing at an entrance of the impactor channel.

14. The apparatus according to claim 12, wherein the conical part is a recessed cone comprising a surface with a tangent having an angle with the main axis of rotational symmetry increasing with a cone radius, admitting substantially the same acute impact angle $\gamma$ for each powder agglomerate meeting the impacting surface.

15. The apparatus according to any claim 1, comprising at least one additional inlet conduit with a projection line that intersects the inlet conduit parallel plane.

16. The apparatus according to of claim 1, further comprising a pressurized gas having a pressure of at least 50 bar in the pressure chamber.

* * * * *

UNITED STATES PATENT AND TRADEMARK OFFICE
CERTIFICATE OF CORRECTION

| | |
|---|---|
| PATENT NO. | : 11,779,944 B2 |
| APPLICATION NO. | : 17/097052 |
| DATED | : October 10, 2023 |
| INVENTOR(S) | : Per Gerde |

It is certified that error appears in the above-identified patent and that said Letters Patent is hereby corrected as shown below:

In the Claims

Claim 1, Column 7, Line 22, after "aerosolizable" delete "a".

Signed and Sealed this
Ninth Day of January, 2024

Katherine Kelly Vidal
*Director of the United States Patent and Trademark Office*